US00PP25931P3

(12) United States Plant Patent
Danziger

(10) Patent No.: US PP25,931 P3
(45) Date of Patent: Sep. 22, 2015

(54) ***PETUNIA* PLANT NAMED 'DRAY68'**

(50) Latin Name: *Petunia sensu wijsman*
Varietal Denomination: DRAY68

(71) Applicant: Gavriel Danziger, Moshav Mishmar Hashiva (IL)

(72) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 7 days.

(21) Appl. No.: 13/986,305

(22) Filed: Apr. 19, 2013

(65) Prior Publication Data

US 2014/0317813 P1 Oct. 23, 2014

(51) Int. Cl.
*A01H 5/02* (2006.01)

(52) U.S. Cl.
USPC ..... Plt./356.1
CPC ..... *A01H 5/02* (2013.01)

(58) Field of Classification Search
USPC ..... Plt./356.1
CPC ..... A01H 5/00
See application file for complete search history.

(56) References Cited

PUBLICATIONS

CPVO, 2013.*
New Varieties Digest, 2012.*

* cited by examiner

*Primary Examiner* — Keith Robinson
(74) *Attorney, Agent, or Firm* — Cassandra Bright

(57) ABSTRACT

A new and distinct *Petunia* cultivar named 'DRAY68' is disclosed, characterized by extra large velvety black flowers. The new variety is vigorous and very well branched as well as abundant in flowering and of a mounded, ball shape. The new variety is a *Petunia*, normally produced as an outdoor garden or container plant.

2 Drawing Sheets

Figure 1:
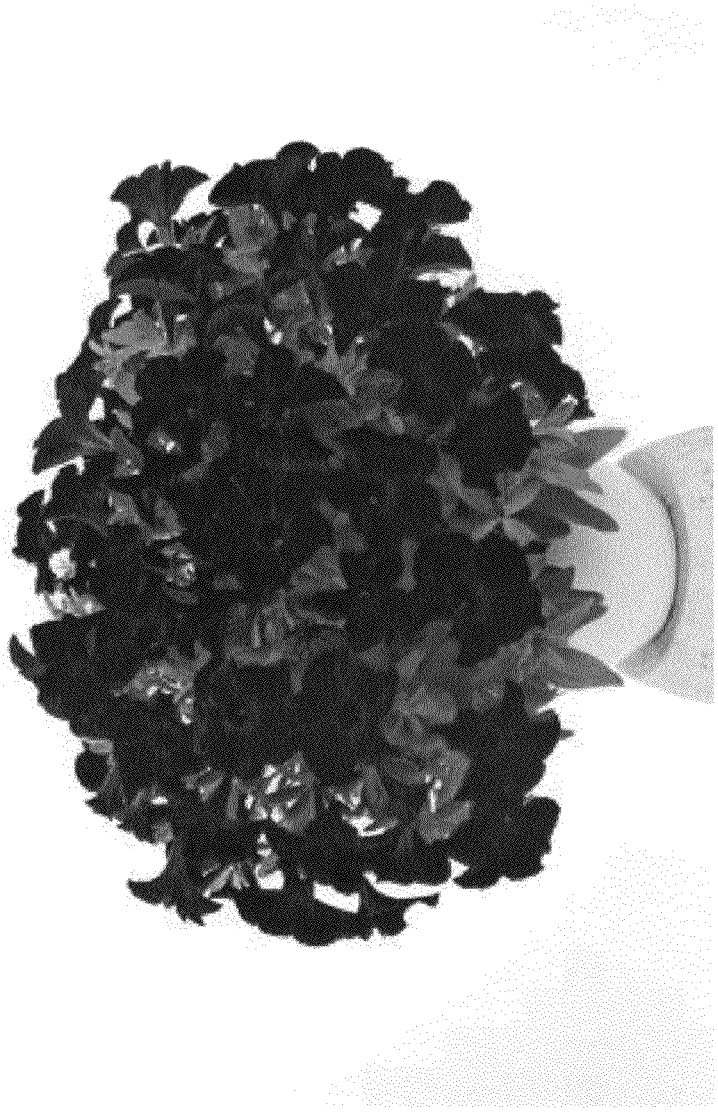

Latin name of the genus and species: *Petunia sensu wijsman.*
Variety denomination:
'DRAY68'.

BACKGROUND OF THE INVENTION

The new *Petunia* cultivar is a product of a planned breeding program conducted by the inventor, Gavriel Danziger, in Moshav Mishmar Hashiva, Israel. The objective of the breeding program was to produce new *Petunia* varieties for ornamental commercial applications. The cross resulting in this new variety was made during October of 2010.

The seed parent is the unpatented non-commercial seedling variety referred to as *Petunia* '9-3078' The pollen parent is the patented variety referred to as *Petunia* 'Balpephan' U.S. Plant Pat. No. 22,440, containing the black gene described in utility patent U.S. Pat. No. 7,642,436. The new variety was discovered in April of 2011 by the inventor in a group of seedlings resulting from the 2010 crossing, in a research greenhouse in Moshav Mishmar Hashiva, Israel.

Asexual reproduction of the new cultivar has been performed by vegetative cuttings. This was first performed at a research greenhouse in Moshav Mishmar Hashiva, Israel in May of 2011 and has shown that the unique features of this cultivar are stable and reproduced true to type in more than 25 generations.

SUMMARY OF THE INVENTION

The cultivar 'DRAY68' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DRAY68' These characteristics in combination distinguish 'DRAY68' as a new and distinct *Petunia* cultivar:

1. Mounded ball shape.
2. Vigorous and very well branched plants.
3. Flower color is velvety black.
4. Flower size is extra large.
5. Abundant flowering.

Plants of the new cultivar 'DRAY68' are similar to plants of the seed parent, *Petunia* '9-3078' in most horticultural characteristics, however, plants of the new cultivar 'DRAY68' are smaller, with more branches than the seed parent. 'DRAY68' also produces an abundant quantity of extra large velvety black flowers whereas the seed parent produces medium size red flowers. Additionally 'DRAY68' produces a mounded ball plant form compared to the semi upright form of the seed parent.

Plants of the new cultivar 'DRAY68' are similar to plants of the pollen parent; *Petunia* 'Balpephan' in most horticultural characteristics, however, plants of the new cultivar 'DRAY68' produce extra large black velvety flowers compared to the large dark purple flowers with yellow stripes of the pollen parent. Also 'DRAY68' produces a very well branched as well as mounded and ball-shaped plant form compared to the medium branched and mounded form of the pollen parent. Additionally, 'DRAY68' flowers more abundantly than the pollen parent.

COMMERCIAL COMPARISON

Plants of the new cultivar 'DRAY68' are similar to the commercial variety *Petunia* 'Balpephan' U.S. Plant Pat. No. 22,440, U.S. Pat. No. 7,642,436, the pollen parent, as compared in paragraph [0007].

Plants of the new cultivar 'DRAY68' can also be compared to the commercial variety *Petunia* 'Balpepin' U.S. Plant Pat. No. 22,414, U.S. Pat. No. 7,642,436. These varieties are similar in most horticultural characteristics; however 'DRAY68' produces larger velvety black flowers compared to the purple flowers with narrow yellow-white stripes of comparator 'Balpepin'. Additionally 'DRAY68' produces a plant with leaves of elliptic shape and narrow width as well as a ball-shaped and very branched plant form compared to the ovate leaves and semi-upright and lesser branched form of comparator 'Balpepin'.

BRIEF DESCRIPTION OF THE PHOTOGRAPHS

The accompanying photograph in FIG. 1 illustrates in full color a typical plant of 'DRAY68' grown in a greenhouse, in a 13 cm pot. Age of the plant photographed is approximately 3 months from a rooted cutting.

Figure 2:
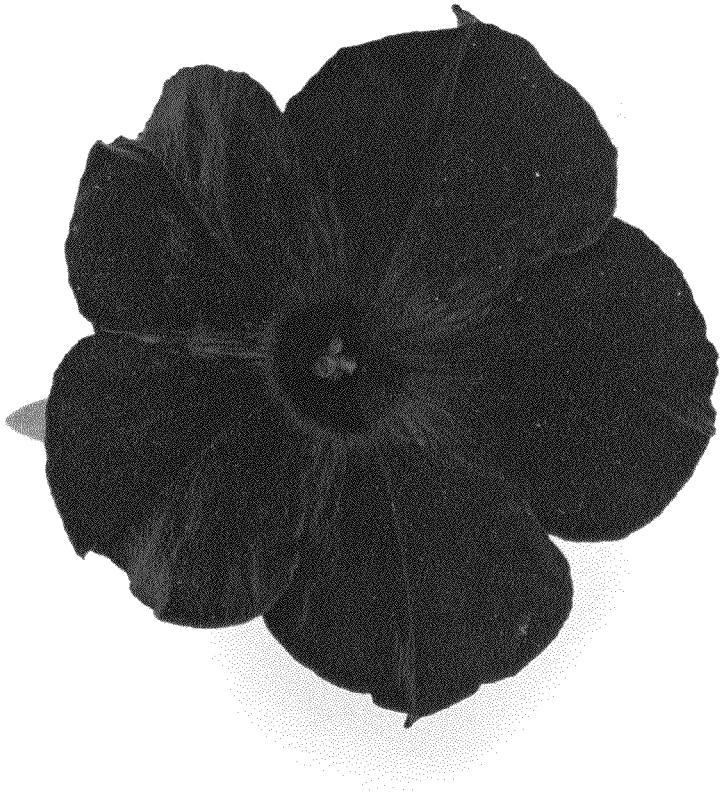

FIG. 2 illustrates in full color a close up of a typical bloom of 'DRAY68'. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DRAY68' plants grown outdoors during, Spring, Summer, and Autumn in Moshav Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia sensu wijsman* 'DRAY68'.

PROPAGATION

Time to initiate roots: About 10 to 14 days.
Root description: Fibrous.

PLANT

Age of plant described: Approximately 60 days from rooted cutting.
Pot size of plant described: 13 cm.
Growth habit: Mounded.
Height: To top of flowers 25 cm.
Plant spread: 30 cm.
Growth rate: Vigorous.
Branching characteristics: Very Branched.
Quantity of primary lateral branches: 8.
Characteristics of primary lateral branches:
- *Form*.—Cylindrical.
- *Length*.—About 40 cm.
- *Diameter*.—About 0.4 cm.
- *Color*.—Yellow-green group 144B RHS.
- *Texture*.—Pubescent.
- *Strength*.—Good.

Internode length: About 2 cm.

FOLIAGE

Leaf:
- *Arrangement*.—Opposite.
- *Quantity*.—Approximately 18 per branch.
- *Average length*.—6.5 cm.
- *Average width*.—2.5 cm.
- *Shape of blade*.—Elliptic.
- *Apex*.—Acute.
- *Base*.—Acute.
- *Margin*.—Entire.
- *Texture of top surface*.—Velvety. Texture of bottom surface: Velvety.
- *Pubescence*.—Pubescent.
- *Aspect*.—90°.
- *Color*.—Young foliage upper side: Yellow-green group 146A RHS. Young foliage under side: Yellow-green group 146B RHS. Mature foliage upper side: Yellow-green group 147A RHS. Mature foliage under side: Yellow-green group 146A RHS.
- *Venation*.—Type: Pinnate. Venation color upper side: Yellow-green group 147B RHS. Venation color under side: Yellow-green group 147C RHS.
- *Petiole*.—Length: About 1 cm. Diameter: About 0.3 cm. Color: Yellow-green group 147B RHS. Texture: Velvety.

FLOWER

Natural flowering season: Spring, Summer & Autumn.
Days to flowering from rooted cutting: About 30 days.
Inflorescence and flower type and habit: Axillary, single flower, salverform shape, erect, outwardly facing flower habit.
Rate of flower opening: 2 to 3 days from bud to fully opened flower.
Flower longevity on plant: 3 to 6 days.
Approximate quantity of flowers per plant: About 80.
Persistent or self-cleaning: Self-Cleaning.
Bud:
- *Shape*.—Tubular.
- *Length*.—About 4.5 cm.
- *Diameter*.—About 0.8 cm.
- *Color*.—Violet-blue group N92A RHS.

Flower size:
- *Diameter*.—About 7 cm.
- *Flower tube length*.—About 3 cm.
- *Flower tube diameter at distal end*.—1.3 cm.
- *Flower tube diameter at proximal end*.—0.4 cm.

Petals:
- *Length from throat*.—About 2 cm.
- *Width*.—About 4 cm.
- *Quantity*.—5.
- *Texture*.—Velvety both upper and lower surfaces.
- *Apex*.—Acute.
- *Margin*.—Entire.
- *Color*.—When opening: Upper surface: Violet-blue group N92A RHS. Lower surface: Violet-blue group N92A RHS. Fully opened: Upper surface: Black group 202A RHS. Lower surface: Violet-blue group N92A RHS. Flower throat (inside): Black group 202A RHS. Flower throat, vein: Black group 202A RHS. Flower tube (outside): Violet-blue group N92A RHS. Flower tube, vein: Yellow-green group 144D RHS. Fading: Petals fading to: Black group 202A RHS — Do not fade.

Calyx/sepals:

*Quantity per flower.*—5.

*Shape*.—Elliptic.

*Length*.—About 2 cm. Corolla tube length: About 1.5 cm.

*Width*.—About 0.6 cm.

*Apex*.—Rounded.

*Base*.—Cuneate.

*Margin*.—Entire.

*Texture*.—Velvety both upper and lower surfaces.

*Color*.—Upper Surface: Yellow-green group 146A RHS. Lower Surface: Yellow-green group 146A RHS.

Peduncle:

*Length*.—About 5 cm.

*Diameter*.—About 0.2 cm.

*Color*.—Yellow-green group 146A RHS.

*Orientation*.—45° degree angle. straight.

Fragrance: None.

REPRODUCTIVE ORGANS

Stamens:

*Number*.—5.

*Filament length*.—About 2.2 cm.

Anthers:

*Shape*.—Rounded.

*Length*.—About 0.2 cm.

*Color*.—Violet-blue group 98D RHS.

Pollen:

*Color*.—Violet-blue group 98D RHS.

*Quantity*.—Abundant.

Pistil:

*Number*.—1.

*Length*.—About 2.2 cm.

*Style*.—Length: About 1.9 cm. Color: Yellow-green group 144A RHS.

*Stigma*.—*Shape: Rounded. Color: Yellow-green group* 144A RHS. Ovary Color: Green group 143B RHS.

OTHER CHARACTERISTICS

Seeds and fruits: About 60 brown, rounded seeds of about 0.5 mm diameter, per one brown conical capsule.

Disease/pest resistance: Neither resistance nor susceptibility to the normal diseases and pest of *Petunia* have been observed. Typical well known diseases include: *Botrytis cineria, Fusarium, Pythium, Phytophthora*, and *Rhizoctonia* species. Typical well know pests include: Leaf miners, spider mites, thrips and possibly caterpillars.

Temperature tolerance: From 5° to 40° C.

What is claimed is:

1. A new and distinct cultivar of *Petunia* plant named 'DRAY68' as herein illustrated and described.

* * * * *